US009048661B2

(12) United States Patent
Zhang

(10) Patent No.: US 9,048,661 B2
(45) Date of Patent: Jun. 2, 2015

(54) BATTERY PROTECTION CIRCUITS

(75) Inventor: Zhibin Zhang, San Jose, CA (US)

(73) Assignee: Apple Inc., Cupertino, CA (US)

( * ) Notice: Subject to any disclaimer, the term of this patent is extended or adjusted under 35 U.S.C. 154(b) by 365 days.

(21) Appl. No.: 13/535,311

(22) Filed: Jun. 27, 2012

(65) Prior Publication Data

US 2014/0002006 A1 Jan. 2, 2014

(51) Int. Cl.
*H02J 7/00* (2006.01)
*G08B 21/00* (2006.01)
*G01N 27/416* (2006.01)
*H02H 7/18* (2006.01)

(52) U.S. Cl.
CPC ................. *H02H 7/18* (2013.01); *G08B 21/00* (2013.01); *G01N 27/416* (2013.01); *H02J 7/0036* (2013.01); *H02J 2007/0037* (2013.01)

(58) Field of Classification Search
CPC ... H02J 7/00; H02J 2007/0037; H02J 7/0036; G08B 21/00; G01N 27/416; H02H 7/18
USPC ......... 320/107, 132, 136, 148, 149, 156, 157, 320/161, 162, 164; 340/636.17; 324/433
See application file for complete search history.

(56) References Cited

U.S. PATENT DOCUMENTS 3,678,368 A * 7/1972 Popp ................................ 363/17
3,893,006 A   7/1975 Algeri et al.
5,066,869 A   11/1991 Neidorff
5,581,170 A * 12/1996 Mammano et al. ........... 320/116
5,631,537 A *  5/1997 Armstrong .................... 320/118
6,028,755 A *  2/2000 Saeki et al. .................. 361/91.1
6,836,100 B2  12/2004 Egan et al.
7,408,396 B2  8/2008 El-Khoury et al.
8,587,257 B2 * 11/2013 Murakami et al. ........... 320/134
2003/0099075 A1 *  5/2003 Pannwitz ......................... 361/90
2005/0145946 A1 *  7/2005 Lee et al. ...................... 257/355
2010/0013324 A1   1/2010 Yamashita et al.
2011/0140669 A1 *  6/2011 Murakami et al. ........... 320/134
2012/0050931 A1 *  3/2012 Terry et al. ................... 361/91.5
2013/0049697 A1 *  2/2013 Li .................................. 320/134
2013/0154543 A1 *  6/2013 Richardson et al. .......... 320/104

* cited by examiner

Primary Examiner — Phallaka Kik
(74) Attorney, Agent, or Firm — Downey Brand LLP

(57) ABSTRACT

An overvoltage battery protection circuit includes a voltage comparator configured to compare a scaled version of a voltage with a voltage reference and indicate an overvoltage condition when the scaled voltage exceeds the voltage reference. The voltage comparator is powered by a first voltage domain. The circuit further includes a first transistor coupled to an output of the voltage comparator and configured to turn on when the voltage comparator indicates the overvoltage condition and generate an overvoltage signal for at least one external device. The circuit further includes a second transistor coupled to the overvoltage signal and configured to turn on when the overvoltage signal is asserted and force the overvoltage signal to remain asserted independent of the first voltage domain. The first and second transistors are powered by a second voltage domain.

24 Claims, 5 Drawing Sheets

BATTERY PROTECTION CIRCUITS

FIELD OF THE DESCRIBED EMBODIMENTS

The described embodiments relate generally to personal electronic devices, and more particularly, to battery protection circuits for personal electronic devices.

BACKGROUND

Generally, high capacity rechargeable batteries are popular choices to power personal electronic devices. Depending upon a particular chemistry of the battery, different over or under-voltage conditions can cause battery failure. For example, in Lithium-ion and Lithium polymer batteries, certain over-voltage conditions may cause battery failure and can result in an explosion. Therefore, the Institute of Electrical and Electronics Engineers (IEEE) has developed a set of standards for rechargeable batteries, in particular IEEE 1725, the entire contents of which are hereby incorporated by reference herein. IEEE 1725 stipulates the necessity for over-voltage protection under a two-component failure. For example, a first failure may include a short circuit across a battery charger (first component) and a second failure may include a failure of a protective circuit integrated with a battery (second component) during the short circuit described above. In this scenario, an appropriate battery protection circuit should be present to overcome the two-component failure.

SUMMARY OF THE DESCRIBED EMBODIMENTS

This paper describes various embodiments that relate to personal electronic devices with rechargeable batteries. In particular, embodiments described herein provide battery protection circuits which overcome and appropriately protect personal electronic devices from component failure in battery charging circuitry.

According to one embodiment of the specification, an overvoltage battery protection circuit includes a voltage comparator configured to compare a scaled version of a voltage with a voltage reference and indicate an overvoltage condition when the scaled voltage exceeds the voltage reference. The voltage comparator is powered by a first voltage domain. The circuit further includes a first transistor coupled to an output of the voltage comparator and configured to turn on when the voltage comparator indicates the overvoltage condition and generate an overvoltage signal for at least one external device. The circuit further includes a second transistor coupled to the overvoltage signal and configured to turn on when the overvoltage signal is asserted and force the overvoltage signal to remain asserted when the first transistor turns off. The first and second transistors are powered by a second voltage domain.

According to another embodiment of the specification, a battery protection system includes a battery charging device, an overvoltage protection integrated circuit (IC) in communication with the battery charging device and configured to receive an overvoltage signal, and an overvoltage battery protection circuit in communication with the battery charging device and the overvoltage protection IC. The overvoltage battery protection circuit includes a voltage comparator configured to indicate an overvoltage condition, and a latch pair of transistors configured to activate in response to the overvoltage condition and force the overvoltage signal to remain asserted until the battery charging device is powered down or replaced.

A method for protecting a rechargeable battery from excessive charging voltage is described. The method is carried out by receiving a first voltage domain, processing the first received voltage domain to produce a second voltage domain, wherein the second voltage domain is coupled to a battery charging circuit and a battery protection circuit, monitoring the second voltage domain with the battery protection circuit, disabling the battery charging circuit through the battery protection circuit when the second voltage domain exceeds a first predetermined voltage, and maintaining the disabling until the first voltage domain is less than a second predetermined voltage.

Other aspects and advantages of embodiments described in the specification will become apparent from the following detailed description taken in conjunction with the accompanying drawings which illustrate, by way of example, the principles of the described embodiments.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one skilled in the art without departing from the spirit and scope of the described embodiments.

DETAILED DESCRIPTION OF SELECTED EMBODIMENTS

Representative applications of methods and apparatus according to the present application are described in this section. These examples are being provided solely to add context and aid in the understanding of the described embodiments. It will thus be apparent to one skilled in the art that the described embodiments may be practiced without some or all of these specific details. In other instances, well known process steps have not been described in detail in order to avoid unnecessarily obscuring the described embodiments. Other applications are possible, such that the following examples should not be taken as limiting.

In the following detailed description, references are made to the accompanying drawings, which form a part of the description and in which are shown, by way of illustration, specific embodiments in accordance with the described embodiments. Although these embodiments are described in sufficient detail to enable one skilled in the art to practice the described embodiments, it is understood that these examples are not limiting; such that other embodiments may be used, and changes may be made without departing from the spirit and scope of the described embodiments.

In one embodiment of a battery protection system, two voltage nodes can be monitored. A first voltage node can be related to, or coupled to a battery, such as a battery charging voltage. A second voltage node can be a voltage related to a voltage supplied by an external charger, such as the ones often used to supply power for portable computing devices or portable media devices.

If the first voltage node exceeds a first voltage level, the battery protection system can disable battery charging. In one embodiment, battery charging can be disabled by asserting a shutdown signal to a battery charging circuit. After the battery charging is initially disabled, battery charging can be maintained as disabled until the second voltage node is below a second voltage level. In one embodiment, the battery charging is disabled until the second voltage node is approximately 0 volts.

By continually disabling battery charging, a user can be required to remove power from the second voltage node, which in some applications can be accomplished by removing power from the external charger. In one embodiment, such a configuration can protect a battery from receiving hazardous voltages when two components within the battery charging path fail.

Figure 1:
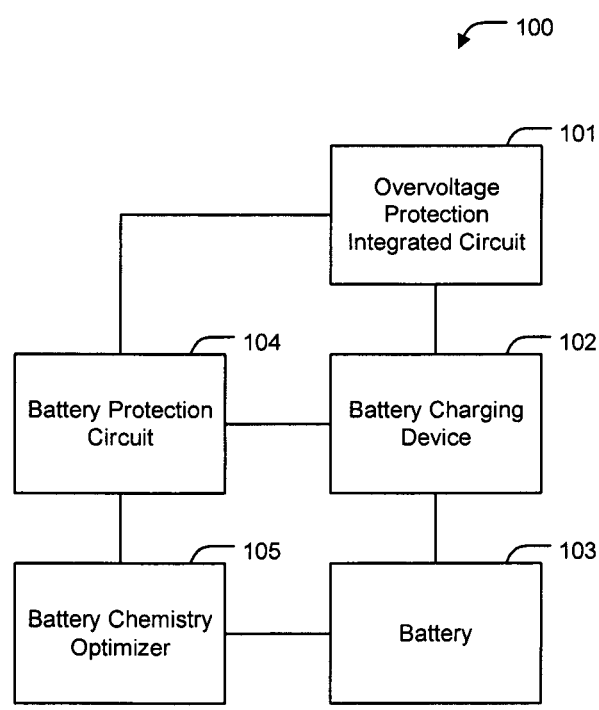
FIG. 1 is a schematic of a battery protection system, according to an exemplary embodiment of the present specification.

Turning to FIG. 1, a schematic of a battery protection system is provided. As illustrated, the system 100 includes overvoltage protection integrated circuit (IC) 101, battery charging device 102 in communication with the overvoltage protection IC 101, and battery 103 in communication with the battery charging device 102.

The system 100 further includes overvoltage battery protection circuit 104 in communication with the overvoltage protection IC 101 and the battery charging device 102. The system further includes battery chemistry optimizer 105 in communication with the battery protection circuit 104 and the battery 103.

The overvoltage protection IC 101 is configured to receive an overvoltage signal from the battery protection circuit 104. The battery protection circuit 104 is configured to generate the overvoltage signal responsive to a comparison of a scaled version of a voltage with a voltage reference. The overvoltage signal is generated if the scaled voltage exceeds the voltage reference. The battery protection circuit 104 is configured to force the overvoltage signal to remain asserted until the battery charging device 102 is powered down or replaced. Responsive to receiving the overvoltage signal, the overvoltage protection IC 101 is configured to turn off a power supply to the battery charging device 102. However, regardless of whether the power supply is turned on or off, the overvoltage signal remains asserted until the battery charging device 102 is powered down or replaced. This may be facilitated through a latch pair of transistors or other suitable configuration.

The battery chemistry optimizer 105 is configured to adjust a reference voltage of the battery protection circuit 104 responsive to battery chemistry information of the battery. Battery chemistry information may be any suitable information, including but not limited to battery type, age, number of charge/discharge cycles, battery chemistry, battery components, or any other desired information. The battery chemistry information may be received directly from the battery 103 or from an external component. The battery chemistry information may be transmitted over a communication interface, for example, a controller area network (CAN) interface, two-wire interface, I²C interface, single wire interface, system management bus (SMB), or any other suitable interface. The adjustment to the reference voltage of the battery protection circuit may enable increased or reduced overvoltage protection dependent upon the battery chemistry. For example, certain battery types or ages may require increased or reduced voltages which may require a different protection scheme. Thus, the adjustment to the reference voltage of the battery protection circuit 104 allows a slight change to the protection scheme while still enabling stable overvoltage protection.

Hereinafter, examples of the battery protection circuit 104 are described in detail below with reference to FIGS. 2-3.

Figure 2:
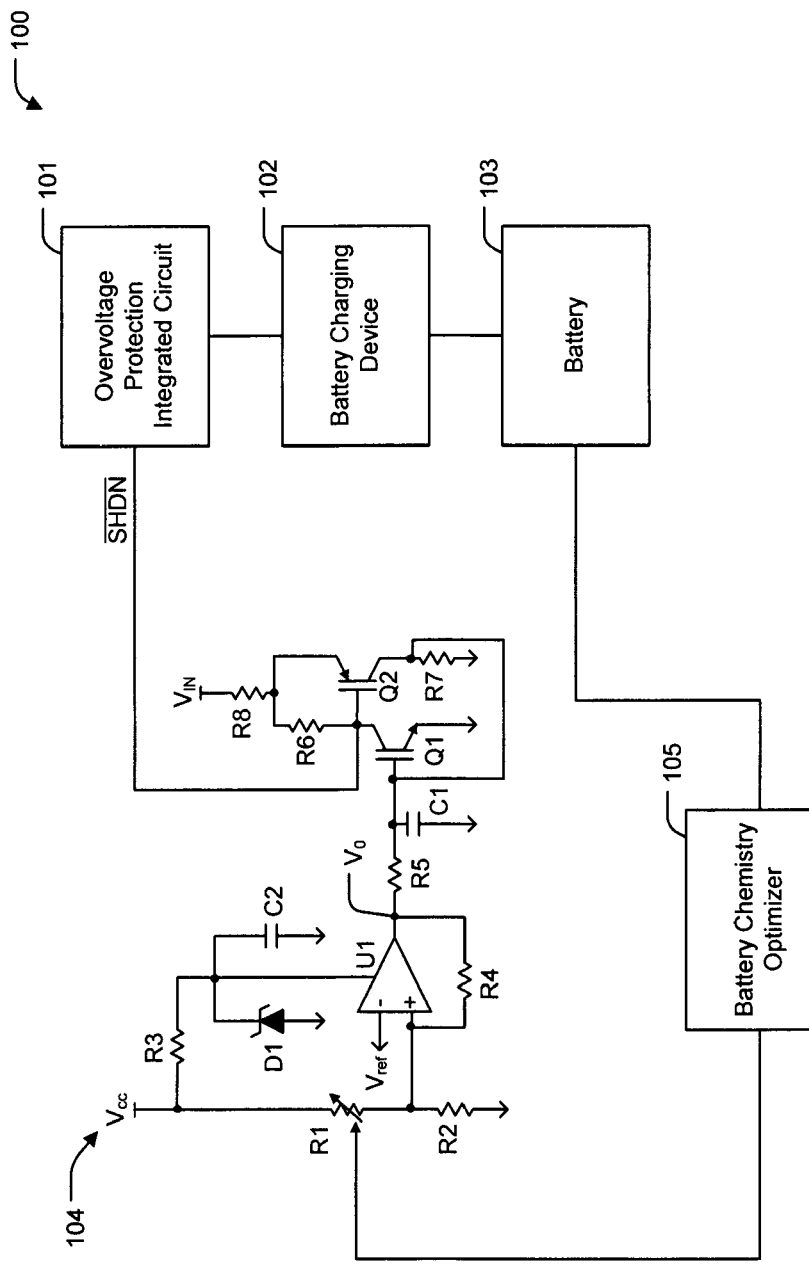
FIG. 2 is a schematic of a battery protection system including a detailed schematic of an overvoltage battery protection circuit, according to an exemplary embodiment of the present specification.
Figure 3:
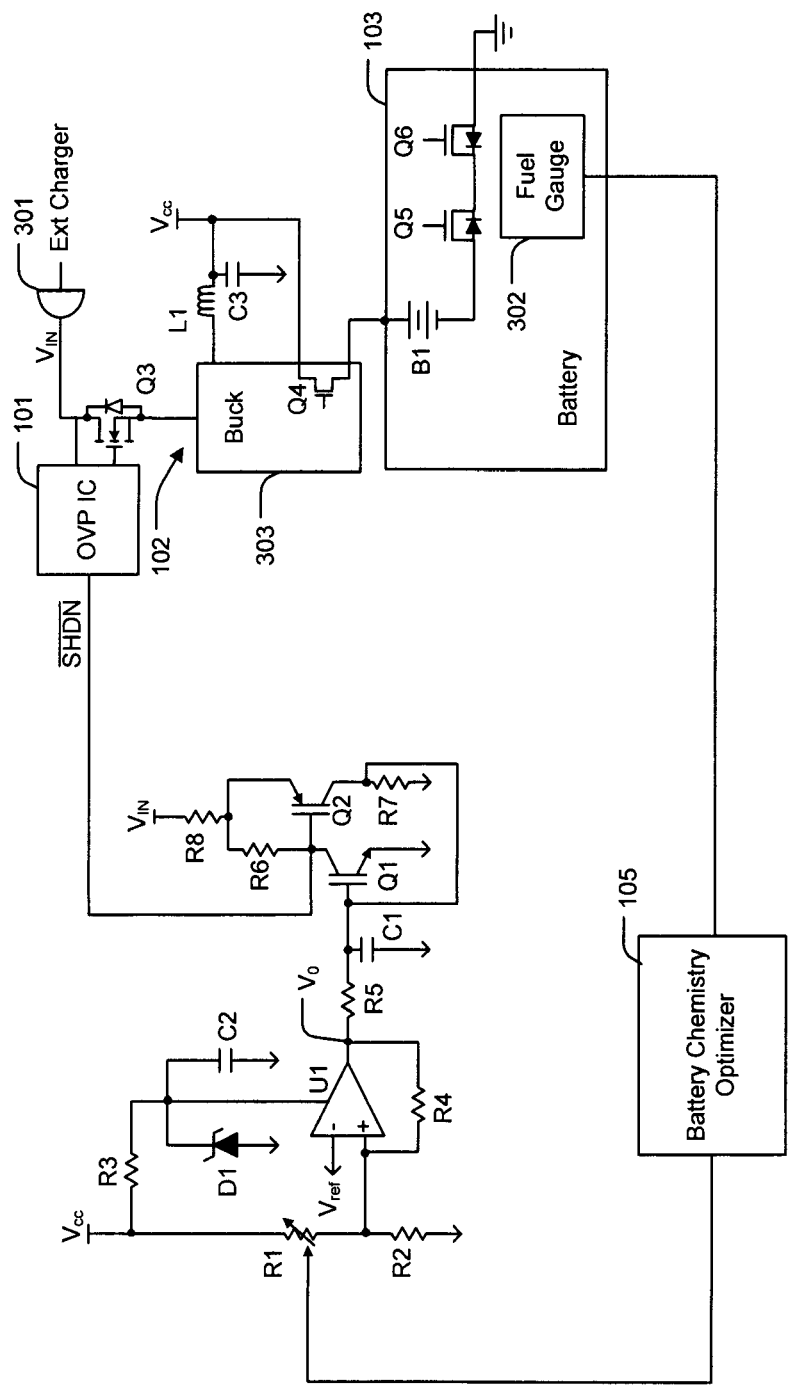
FIG. 3 is a schematic of a battery protection system including a detailed schematic of an overvoltage battery protection circuit and a detailed schematic of a battery charging device, according to an exemplary embodiment of the present specification.
Figure 4:
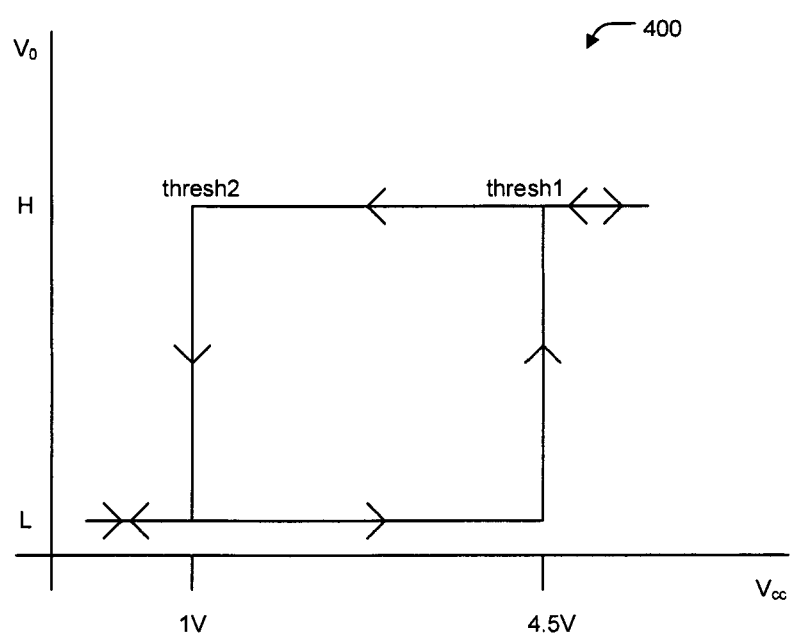
FIG. 4 is graph of hysteresis of a battery protection circuit, according to an exemplary embodiment of the present specification.

As shown in FIG. 2, the battery protection circuit 104 includes voltage comparator U1. Voltage comparator U1 is configured to have a particular amount of hysteresis (e.g., see FIG. 4). The voltage comparator U1 is configured to compare a scaled version of voltage $V_{CC}$ with voltage reference $V_{ref}$ and indicate an overvoltage condition when the scaled voltage exceeds the voltage reference. The voltage comparator is powered by a first voltage domain $V_{CC}$ provided by the battery charging device 102. The scaling of the voltage $V_{CC}$ is facilitated through resistors R1 and R2. According to one embodiment, resistor R1 is a variable resistor configured to be adjusted by the battery chemistry optimizer 105. For example, the resistance seen at resistor R1 may be altered based on battery chemistry information as described above. In this manner, the scaling of voltage $V_{CC}$ is adjusted to take into consideration different battery chemistry, age, and other suitable information. The reference voltage $V_{ref}$ may be any suitable voltage based on a desired threshold for overvoltage signal generation. According to one embodiment, an appropriate value for the reference voltage $V_{ref}$ is between about 1 and 1.2 Volts. In yet another embodiment, the reference voltage $V_{ref}$ can be determined by a band-gap reference.

As further illustrated the powering of the comparator U1 is facilitated through resistor R3, diode D1 and decoupling capacitor C2. Furthermore, positive feedback, loop gain, and therefore hysteresis is facilitated through resistors R4 and R5, and capacitor C1. The hysteresis as present between reference point $V_0$ and $V_{CC}$ is illustrated in detail in FIG. 4.

As further illustrated, the battery protection circuit 104 also includes a latched pair of transistors Q1 and Q2 powered from a second voltage domain $V_N$ provided from an external charger. The transistor Q1 may be an NPN bipolar junction transistor and the transistor Q2 may be a PNP bipolar junction transistor, according to one embodiment. As shown resistor network comprising resistors R6, R7, and R8 biases the transistors Q1 and Q2 such that when transistor Q1 is turned on (e.g., due to overvoltage), the overvoltage signal $\overline{SHDN}$ is generated. Furthermore, the overvoltage signal $\overline{SHDN}$ will remain asserted by transistor Q2 until $V_N$ falls below a predetermined threshold condition. For example, $V_N$ would fall below the predetermined threshold condition if an external charger supplying current to the battery charging device 102 were shutdown, removed, or replaced.

As described above, the first transistor Q1 is coupled to an output of the voltage comparator U1 and configured to turn on when the voltage comparator U1 indicates an overvoltage condition. At this stage, the first transistor Q1 generates the overvoltage signal $\overline{SHDN}$. Furthermore, the second transistor Q2 is coupled to the overvoltage signal $\overline{SHDN}$ and configured to turn on when the overvoltage signal is asserted. The second transistor Q2 forces the overvoltage signal $\overline{SHDN}$ to remain asserted until $V_{IN}$ falls below a predetermined threshold value.

Hereinafter, a more detailed description of the battery charging device 102 is provided with reference to FIG. 3.

As illustrated, the battery charging device 102 may include an external power metal-oxide-semiconductor field effect transistor (MOSFET) Q3 coupled to external charger 301. The external charger 301 provides $V_N$ as described above. The transistor Q3 is controlled by overvoltage protection IC 101 such that the overvoltage protection IC 101 may shut down power to charging buck 303. The battery charging device 102 further includes inductance L1 and capacitor C3 configured to supply voltage $V_{CC}$ for powering the comparator U1.

As further illustrated, the charging buck 303 can include at least one linear charging element Q4. The linear charging element may, according to one embodiment, be a power MOSFET.

As further illustrated, battery 103 may include at least one storage element B1 coupled to an output of the linear charging device Q4. Therefore, an output of the linear charging device Q4 may charge the storage element B1 as controlled through switching devices Q5 and Q6. Switching devices Q5 and Q6 may be embodied as power MOSFETS or any other suitable devices. Switching devices Q5 and Q6 may be controllably turned on/off depending upon a charge state as indicated by fuel gauge 302 or by an external or internal controller (not illustrated).

Furthermore, the fuel gauge 302 may provide battery charge state information to the battery chemistry optimizer 105 such that overvoltage protection values are adjusted. This may be in addition or in combination with the battery chemistry information provided by battery 103. Thus, the battery protection circuit 104 may be adjusted according to whether a battery is entirely discharged, partially charged, mostly charged, or above a threshold charge state. In this manner, better overvoltage protection may be afforded.

Figure 5:
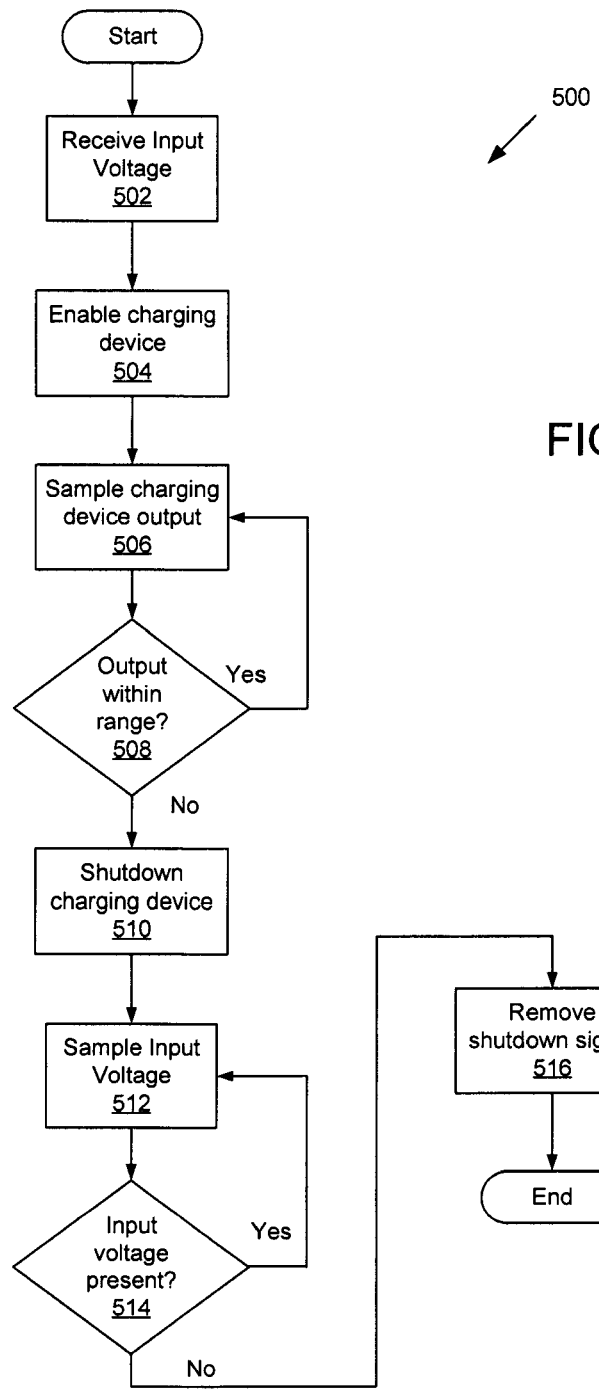
FIG. 5 is a flow chart of method steps for protecting a battery from excessive charging voltage in accordance with one embodiment of the specification.

FIG. 5 is a flow chart of method steps for protecting a battery from excessive charging voltage 500 in accordance with one embodiment of the specification. Persons skilled in the art will understand that any system configured to perform the method steps in any order is within the scope of this description. The method described herein can be provided by analog type circuits as shown in FIGS. 2 and 3, digital type circuits including analog to digital converters, digital to analog converters, state machines, embedded processors, processors and/or memory. In some embodiments, the method described herein can be provided by a processor executing instructions.

The method begins in step 502 where the input voltage is received. In one embodiment, this input voltage can be an input voltage that can be provided by the external charger 301 that can receive a relatively high line voltage (such as 110 volts) and provide a relatively lower voltage such as 15 volts. In one embodiment the external charger 301 can provide direct current (DC) voltage. In another embodiment, the external charger 301 can provide alternating current (AC).

The method proceeds to step 504 where the charging device is enabled. For example, battery charging device 102 as shown in FIG. 1 or charging device 303 can be enabled. In one embodiment, charging device 303 supply power to charge the battery 103 while also supplying power for one or more circuits such as battery protection circuit 104. In step 506, the output of the charging device, such as charging device 303 can be monitored. In one embodiment, monitoring can be provided by an analog type of circuit such as comparator U1, or a digital type of circuit such as an analog to digital converter, preferably with an associated sample and hold circuit. In one embodiment, step 506 can monitor the output of the charging device 303 by comparing the output of the charging device 303 to a voltage reference. For example, one output of charging device 303 can be scaled (as through a voltage divider), and that scaled voltage can be compared to the voltage reference. This voltage scaling can advantageously allow accommodation of different voltages from the charging device 303 to be compared with a fixed voltage reference, such as a band-gap voltage reference.

In step 508, if the output of the charging device 303 is within range (i.e., the supplied voltage from charging device 303 is within a proper operating level), then the method can return to step 506. On the other hand, if the output of the charging device 303 is out of operating range, then in step 510, the charging device 303 can be shutdown. In one embodiment, charging device 303 can be disabled by disrupting a supply voltage to charging device 303 such as through over voltage protection IC 101. A shutdown signal can be provided by battery protection circuit 104 to over voltage protection IC 101. In one embodiment, the shutdown signal can be provided by a latching circuit that can assert a shutdown signal, but does not allow the shutdown signal to be de-asserted unless all power is removed from the circuit.

The method proceeds to step 512 when an input voltage is monitored. In one embodiment, the input voltage can be $V_N$ supplied by external charger 301. In step 514, if there is an input voltage present, then the method returns to step 512. On the other hand, if there is no input voltage present ($V_N$ is effectively 0 volts), then in step 516 charging device 303 can be enabled and the method ends. In one embodiment, the shutdown signal can be de-asserted to enable charging device 303.

The various aspects, embodiments, implementations or features of the described embodiments can be used separately or in any combination. Various aspects of the described embodiments can be implemented by software, hardware or a combination of hardware and software. The described embodiments can also be facilitated through computer readable code on a computer readable medium for controlling manufacturing operations or as computer readable code on a computer readable medium for controlling a manufacturing line. The computer readable medium is any data storage device that can store data which can thereafter be read by a computer system. Examples of the computer readable medium include read-only memory, random-access memory, CD-ROMs, HDDs, DVDs, magnetic tape, and optical data storage devices. The computer readable medium can also be distributed over network-coupled computer systems so that the computer readable code is stored and executed in a distributed fashion.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

What is claimed is:
1. An overvoltage battery protection circuit, comprising:
  a voltage comparator configured to compare a scaled voltage with a reference voltage and indicate an overvoltage condition if the scaled voltage exceeds the reference voltage, wherein the voltage comparator is powered by a first voltage domain provided by a first power supply;

a first transistor coupled to an output of the voltage comparator and configured to: turn on when the voltage comparator indicates the overvoltage condition, and provide an overvoltage signal; and a second transistor configured to receive the overvoltage signal, turn on when the overvoltage signal is asserted, and provide the overvoltage signal when the first transistor turns off, wherein the first transistor and the second transistor are powered by a second voltage domain provided by a second power supply different than the first power supply, and the second transistor limits the overvoltage signal when the second voltage domain reaches or falls below a threshold value.

2. The overvoltage battery protection circuit of claim 1, wherein the first transistor is an NPN transistor.

3. The overvoltage battery protection circuit of claim 1, wherein the second transistor is a PNP transistor.

4. The overvoltage battery protection circuit of claim 1, wherein the first power supply is a charging buck.

5. The overvoltage battery protection circuit of claim 1, wherein the second power supply is an external charger.

6. A battery protection system, comprising:
a battery charging device;
an overvoltage protection integrated circuit (IC) in communication with the battery charging device and configured to receive an overvoltage signal; and
an overvoltage battery protection circuit in communication with the battery charging device and the overvoltage protection IC, the overvoltage battery protection circuit comprising:
a voltage comparator powered by a first power supply, wherein the voltage comparator is configured to indicate an overvoltage condition, and
a set of transistors powered by a second power supply, wherein the set of transistors includes at least:
a first transistor configured to provide the overvoltage signal in response to the overvoltage condition; and
a second transistor configured to: provide the overvoltage signal when the first transistor turns off during the overvoltage condition, and limit the overvoltage signal when the battery charging device is powered down or replaced.

7. The battery protection system of claim 6, further comprising:
a battery in communication with the battery charging device.

8. The battery protection system of claim 7, wherein the battery charging device is configured to cease charging the battery in response to the overvoltage signal.

9. The battery protection system of claim 7, further comprising:
a battery chemistry optimizer in communication with the battery and the overvoltage battery protection circuit, the battery chemistry optimizer being configured to adjust a reference voltage of the voltage comparator responsive to battery chemistry information of the battery.

10. The battery protection system of claim 7, wherein the battery is a Lithium-ion battery or a Lithium polymer battery.

11. The battery protection system of claim 6, wherein the comparator is electrically coupled to a voltage divider circuit configured to scale a first power supply voltage.

12. The battery protection system of claim 11, wherein the first power supply is a linear charging element configured to provide a charging voltage.

13. The battery protection system of claim 12, wherein the linear charging element is a power metal-oxide-semiconductor field effect transistor.

14. The battery protection system of claim 6, wherein the voltage comparator is configured to compare a scaled voltage with a reference voltage and indicate the overvoltage condition when the scaled voltage exceeds the reference voltage.

15. The battery protection system of claim 6, wherein the first transistor and the second transistor each correspond to different transistor types.

16. The battery protection system of claim 15, wherein the second power supply is voltage domain is an external battery charger.

17. The battery protection system of claim 6, wherein the first transistor is coupled to an output of the voltage comparator.

18. The battery protection system of claim 17, wherein the second transistor is configured to turn on when the overvoltage signal is asserted.

19. The battery protection system of claim 18, wherein the first transistor is an NPN transistor and the second transistor is a PNP transistor.

20. The battery protection system of claim 6, further comprising:
a battery in communication with the battery charging device; and
a battery chemistry optimizer in communication with the battery and the overvoltage battery protection circuit, the battery chemistry optimizer being configured to adjust a reference voltage of the voltage comparator responsive to battery chemistry information of the battery.

21. A computing device including a protective circuit, the protective circuit comprising:
a voltage comparator configured to indicate an overvoltage condition if an input voltage exceeds a reference voltage, wherein the voltage comparator is powered by a first power supply; and
a first transistor and a second transistor each powered by a second power supply different than the first power supply, wherein:
the first transistor is coupled to an output of the voltage comparator and the first transistor is configured to:
turn on when the voltage comparator indicates the overvoltage condition, and generate an overvoltage signal; and
the second transistor is configured to:
receive the overvoltage signal,
turn on when the overvoltage signal is asserted,
provide the overvoltage signal when the first transistor turns off, and
limit the overvoltage signal when a voltage of the second power supply reaches or falls below a threshold value.

22. The computing device of claim 21, wherein the first transistor is an NPN transistor.

23. The computing device of claim 21, wherein the first power supply is a charging buck.

24. The computing device of claim 21, wherein the second power supply is an external charger.

* * * * *